United States Patent
Gerhold

(10) Patent No.: US 9,535,045 B2
(45) Date of Patent: Jan. 3, 2017

(54) LOW PRESSURE BIOGAS SAMPLE TAKEOFF AND CONDITIONING SYSTEM

(71) Applicant: Mustang Sampling, LLC, Ravenswood, WV (US)

(72) Inventor: Walter F. Gerhold, Dallas, NC (US)

(73) Assignee: Mustang Sampling LLC, Ravenswood, WV (US)

( * ) Notice: Subject to any disclaimer, the term of this patent is extended or adjusted under 35 U.S.C. 154(b) by 312 days.

(21) Appl. No.: 14/305,130

(22) Filed: Jun. 16, 2014

(65) Prior Publication Data

US 2015/0362468 A1  Dec. 17, 2015

(51) Int. Cl.
*G01N 1/00* (2006.01)
*G01N 33/00* (2006.01)

(52) U.S. Cl.
CPC ........ *G01N 33/0016* (2013.01); *G01N 33/004* (2013.01); *G01N 33/0044* (2013.01)

(58) Field of Classification Search
USPC ....................................... 73/28.04
See application file for complete search history.

(56) References Cited

U.S. PATENT DOCUMENTS

| | | | |
|---|---|---|---|
| 4,409,102 A | 10/1983 | Tanner | |
| 6,042,634 A * | 3/2000 | Van Tassel | G01N 1/2258 95/117 |
| 7,416,644 B2 * | 8/2008 | Bonde | B01D 3/346 202/155 |
| 7,883,884 B2 * | 2/2011 | Bonde | A01C 3/00 435/236 |
| 8,158,378 B2 * | 4/2012 | Mitariten | C12P 5/02 435/167 |
| 8,318,476 B2 * | 11/2012 | Parker | B01D 53/84 435/176 |
| 8,713,995 B2 * | 5/2014 | Thompson | F17C 6/00 73/61.55 |
| 2008/0134754 A1 | 6/2008 | Funk | |
| 2011/0189746 A1 | 8/2011 | Mitariten | |
| 2012/0000357 A1 | 1/2012 | Roe et al. | |
| 2012/0122196 A1 | 5/2012 | Johnson | |
| 2012/0180389 A1 | 7/2012 | Knaebel | |
| 2015/0024452 A1 * | 1/2015 | Matelich | C12P 5/023 435/168 |
| 2015/0290575 A1 * | 10/2015 | Rothermel | C10L 3/101 95/148 |

OTHER PUBLICATIONS

Kimmel, K. Techniques for Natural Gas Composite Sampling. Proceedings American School of Gas Measurement Technology. 2003 pp. 65-69.
Siemens AG. Analytical Application Sets. 2013 pp. 4/1-4/56.
GE. Sample Systems for Gas and Moisture Analyzers. Sensing & Inspection Technologies. 2008, pp. 1-4.
International Application No. PCT/US2014/042610, Notification of Transmittal of the International Search Report and the Written Opinion of the International Searching Authority, or the Declaration, dated, Oct. 24, 2014.

* cited by examiner

*Primary Examiner* — Clayton E Laballe
*Assistant Examiner* — Warren K Fenwick
(74) *Attorney, Agent, or Firm* — Cahn & Samuels, LLP

(57) ABSTRACT

A temperature and pressure regulating biogas sample extraction system and method for providing a conditioned biogas sample for constituent analysis.

17 Claims, 4 Drawing Sheets

LOW PRESSURE BIOGAS SAMPLE TAKEOFF AND CONDITIONING SYSTEM

FIELD OF INVENTION

This invention relates to a multi-stage sample conditioning system particularly adapted for use with low pressure biogas sources. The system includes one or more sample take-off probes disposed at different stages during processing of the biogas along points along contingent on the intended use of the gas.

Following extraction of the gas from the source whether at positive or negative pressure, it is passed through a conditioning heater to raise the temperature of the extracted gas sample, heated conduits for communicating the gas to a dryer for removal of water vapor, a compressor and pressure regulator for increasing gas pressure of the now-dried and heated sample to an acceptable level for introduction into one or more appropriate sample analyzers. The system is adapted to prevent the loss of components other than water, e.g., methane, siloxanes, and bioreactor-generated VOCs.

BACKGROUND

Biogas, also referred to as bio-methane, swamp gas, landfill gas, and digester gas, is the product of anaerobic digestion, e.g., the decomposition of waste material without the presence of oxygen which yields predominantly methane and carbon dioxide. After proper processing to appropriate purity, captured biogas is readily usable as a green/renewable fuel for facility heating, electrical power co-generation, and as vehicle fuel for natural gas powered vehicles. Use of such captured "waste" gas as fuel to power electrical generators, charge fuel cells, and the like, is becoming increasingly more common as the economics for the capital expenditures spurred by environmental concerns, recycling, and use of green energy sources are now justified. However, to date, adequate technology addressing the sample conditioning of biogas extracted from the typical low pressure (<1 psig) sources such as biodigesters does not exist.

Several generation and collection sources of biogas exist across a wide range of disciplines, i.e., waste water treatment, solid waste/land fill disposal and management, food processing plants, and the agricultural industry, including processing farm animal waste.

Probably one of the most common and familiar biogas generation and collection sources is from landfills. Advances have been made to promote biogas generation from those sources. For example, one process involves locating a system of pipes in the landfill to inject air into select land fill strata, effectively comprising an in situ digester/bio reactor. The injected air increases the decomposition rate of the land fill solids with a resulting increase in the production rate of methane containing biogas.

The quality and quantity of generated biogas, as would be expected, is based part, on the nature of its source. For example, studies have shown biogas production from a small landfill would be expected to produce over a million standard cubic foot per day (1,238,000 scfd or 35 cmd) for approximately 20 years. Waste water plants (sewage) produce 1.0 cf of digester gas per 100 gallons of waste water per person (2.8 cm). In the agricultural field, a single dairy cow generates the prodigious quantity of 100 cf of digester gas per day (2.8 cmd).

As noted above, anaerobic digestion (bacterial digestion carried out in the absence of oxygen) produces biogases typically from in situ digestion (e.g., landfills) or anaerobic digester systems. Biogases generated from anaerobic digestion contain a mixture of burnable hydrocarbon gas, (methane), VOC's, hydrogen sulfide, siloxanes including Volatile Methyl Siloxanes (VMS), water, and water vapor. A cubic foot of methane has an energy capacity of 1020 BTU (~36,000/cm). Therefore, when a biogas stream is composed of 50 to 60% methane, the heat value of that gas approximates 500-600 BTU/lcf (up to ~24,000/cm).

Before it can be used effectively as a fuel source, however, biogas must be processed. Such processing requires removal and/or minimization of typical impurities found in the biogas output stream. The cleaning begins with particulate removal, followed by removal of water, and, when the desired end product is intended to provide a high quality gas stream, $H_2S$, sulfur species, siloxanes, $CO_2$, digestion generated VOCs (Volatile Organic Chemicals) and oxygen content. The resulting gas is blown, under pressure through a suitable conduit, e.g., 18 inch pipe, to a storage container or directly to a utilization source (heat furnace, fuel cell, etc.). Subject to required purity standards, the resulting cleaned gas may also be utilized independently, blended with local pipeline gas, and even pressurized for use as CNG (Compressed Natural Gas) for powering vehicles.

The level and degree of processing of biogas can also vary based on the intended use of the biogas. For example, if nothing more, entrained water must be removed before biogas can be burned, and the effective removal thereof confirmed by sensor based-analysis. More modern designs of digesters/bioreactors produce biogas with reduced VOCs but increased $H_2S$ in the stream. Removal of the $H_2S$ "pollutant" is critical to use of the biogas in all applications except plant heating. Another newer technology involves conversion of biological material in waste water to electricity via a microbial fuel cell. Due to the sensitive chemistry involved in fuel cells, higher gas purity and therefore, a more rigorous level of biogas cleaning is necessary prior to being used to power the fuel cells.

If intended for use in combustion engines, substantial removal of Hydrogen Sulfide and siloxanes from the biogas is necessary and operationally critical. Failure to achieve such siloxane removal leads to damage resulting from formation of silica-based deposits and coatings on engine components. Effective removal thereof requires confirmation by sensor based-analysis.

Higher purity requirements can also be found in the use of biogas qualified for blending with other pipeline gases and or as compressed natural gas (CNG). In such cases, the gas must be dried and Carbon Dioxide removed. The highest purity requirements are established by standards such as ISO 15404-2006 in where, in addition to the above scrubbing steps, the removal of all moisture is necessary and the gas compressed to high pressures (6,000 psig) for use as Natural Gas Vehicle (NGV) fuel or compressed natural gas (CNG). The success of such processing must again be confirmed through sample takeoff and analysis.

Consequently for industrial biogas utilization, systems sensor/analyzer technology must be used to confirm to measure the composition of the feed gas and processed gas and to confirm that the cleaning steps have been successful.

SUMMARY OF INVENTION

It is an object of the present invention to provide a sample collection, conditioning, and analysis system adaptable for utilization in the case of a selectable biogas stream.

It is another object of the present invention to provide a novel sample conditioning system particularly suited for low pressure biogas generating facilities.

Another object of the present invention is to provide an integrated solution for the conditioning and analysis of low pressure biogas samples.

A further object of the present invention is to provide greater flexibility in the design of a sampling and conditioning system allowing for multi-stream take-off biogas sample analysis.

Still another object of the present invention is to provide a system and method providing essentially real time comparative analysis of a raw biogas feed stock and cleaned biogas.

Yet another object of the invention is to provide an integrated sample conditioning system particularly adapted for low pressure biogas conditioning.

These and other objects are satisfied by a system for conditioning and analyzing a low pressure biogas pipeline stream where the biogas contains one or more contaminants selected from the group consisting of $H_2O$, $CO_2$, $H_2S$, $NH_3$, $C_2H_2$, siloxanes, VOC, and $O_2$ intermixed with $CH_4$, said system, comprising: at least a first gas pipeline takeoff probe for extracting a biogas sample, a heated probe housing, a biogas communication line limiting dew point dropout of the biogas sample conveying the heated biogas sample to a solenoid controlled valve switch and into a sample analyzer cabinet; a gas dryer unit for receiving the extracted biogas sample; a pump and a pressure regulator for increasing the pressure of the heated biogas sample exiting the gas dryer; a gas analyzer unit for measuring the quantity of a contaminant selected from the group consisting of $H_2O$, $CO_2$, $H_2S$, $NH_3$, $C_2H_6$, siloxanes, VOC, and $O_2$ present in the dried and pressurized and heated, biogas sample; a source of compressed industrial grade purge gas input said purge gas being passed through a pressure regulator to said gas dryer unit and said gas analyzer unit; and a gas exhaust for venting the analyzed biogas sample.

Other objects are satisfied by a system for conditioning and analyzing a sample extracted from at least one stream of a biogas where the biogas contains one or more contaminants selected from the group consisting of $H_2O$, $CO_2$, $H_2S$, $NH_3$, $C_2H_6$, siloxanes, VOC, and $O_2$ intermixed with $CH_4$, said system, comprising: at least a first gas pipeline takeoff probe for extracting a low pressure biogas sample, a heated probe housing, a biogas communication line limiting dew point dropout of the biogas sample conveying the heated biogas sample to a solenoid controlled valve switch and into a sample analyzer cabinet; a first pump and a first pressure regulator for increasing the pressure of the heated gas sample for introduction into a gas dryer unit; a second pump and a second pressure regulator for further increasing the pressure of the heated gas sample exiting the dryer; a gas analyzer unit for measuring the quantity of a contaminant selected from the group consisting of $H_2O$, $CO_2$, $H_2S$, $NH_3$, $C_2H_6$, siloxanes, VOC, and $O_2$ present in the dried and pressurized and heated, biogas sample; a source of compressed industrial grade purge gas input gas passed through a pressure regulator to gas dryer unit and said gas analyzer unit; and a gas exhaust for venting the analyzed biogas sample.

Still other objects are satisfied by the method of for conditioning a biogas sample for confirmation of its quality, comprising the steps of: extracting a biogas sample from a select source; regulating the temperature and pressure of the extracted biogas sample; feeding the pressure and temperature regulated biogas sample into a dryer for removal of moisture; increasing the pressurize of the biogas sample output from the dryer; and feeding said biogas sample to a dryer gas component analyzer for measuring the component in the biogas sample.

The present invention provides a low pressure biogas sample conditioning system for confirmation of the quality of scrubbed, cleaned biogas. In effect, it mimics by parallel processing the scrubbing, filtering, and drying stages of the "industrial" biogas stream.

After being drawn by vacuum from its source, e.g., landfill/digester, the raw biogas is fed into a knock-out drum to remove entrained water/liquids. The raw gas is then pressurized from low, if not negative pressure, with a blower to a low pressure, up to about 10 psig but preferably between 5-7 psig. Heat generated by the compression of the gas is removed by a heat exchanger and additional moisture removed using a coalescing filter. This process effectively corresponds to the first step of processing biogas which then is capable for use as a furnace fuel (plant heating). If desired, a sample may be extracted from the slightly pressurized biogas stream by a heated probe enclosure which elevates the temperature of the gas sample to a level preventing Joule-Thompson condensation/dew point dropout (and concomitant loss of gas components) and through heated tubing (preferably either utilizing heat tracing or including vacuum jacketed tubing) to provide thermal stability and avoid dew point dropout during transit to the associated analyzer unit. The analyzer unit contains a dryer and one or more gas analyzers for $H_2S$, sulfurous species, siloxanes, $CO_2$, VOCs, $O_2$ and/or moisture content. The sample is directed under pressure via solenoid valve switch to the appropriate gas analyzer sub-unit.

Sample conditioning of mid-level biogas typically entails selective sampling of the gas stream before sulfur and siloxane scrubbing and following such scrubbing and removal of particulates via filtration. In this case a stream of extracted biogas is sampled before the scrubbing processes and filtered for particulate removal. Selective pressurization and biogas stream selection is achieved with an array of interconnected pumps, pressure regulators, filters and solenoid actuated valves. Calibration gas/air for each of the respective analyzer sub-components follows a dedicated path from its respective discrete supply (tank or compressor) to the respective analyzer sub-component inlet.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings, and which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION

Figure 1:
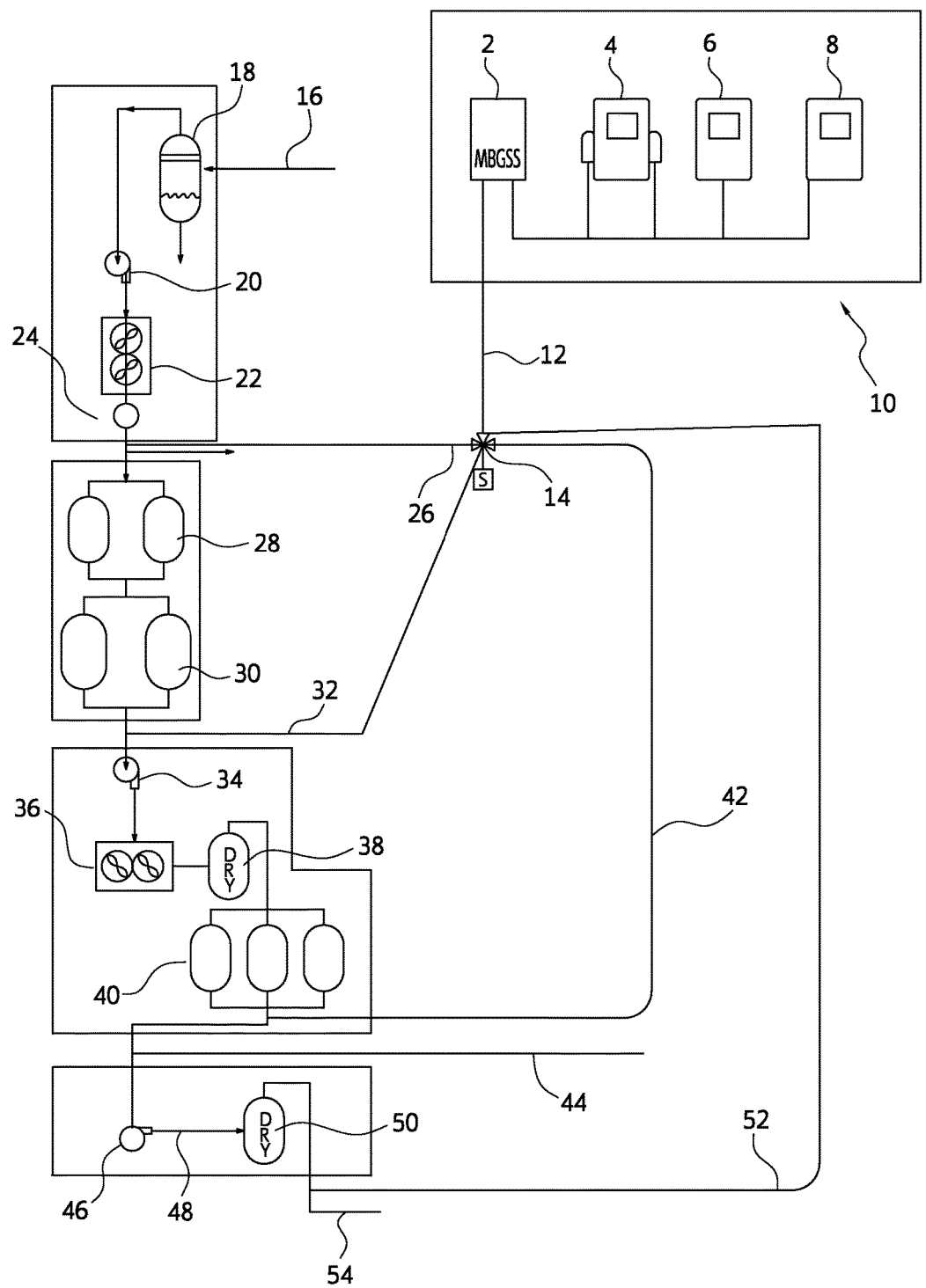
FIG. 1 is a process flow diagram for generation of progressively purified biogas processing output qualities incorporating an embodiment of the invention for selective analysis at select stages.

Referring to the embodiment of FIG. 1, the process flow of a system conforming to an embodiment of the invention employed in the context of a digester and represented diagrammatically. The present invention is intended to provide a biogas processor the capacity for selective takeoff and analysis from a specified output. FIG. 1 illustrates a biogas sample conditioning analyzer unit 10 that integrates all of appropriate drying pressure-regulating and conditioning sub-unit 2, and gas analyzers 4, 6, and 8 which are selective for one or more of the group consisting of contaminants $H_2O$, $CO_2$, $H_2S$, $NH_3$, siloxanes, VOCs, and $O_2$, and non-contaminant $CH_4$. The choice of the analyzers 4, 6, and 8 is dictated by and contingent on the intended scope of analysis required by the installation or user. Based on a user's particular requirements, one or more conventional gas analyzer types may be incorporated such as a Tunable Laser Diode (TLD), a Photo Ionization detector (PID), a Flame Ionization detector (FID), an InfraRed (IR), a Fourier-Transform InfraRed (FT-IR), etc.

The unit 10 is connected via a gas input feed line 12, the input selection of which is determined by the multi-input solenoid valve 14 controlled flow from the respective outputs of biogas at particular stages of treatment.

Although the flow diagram FIG. 1 depicts four discrete stages, depending on the intended use of the processed biogas a particular processor, fewer processing stages may be employed. The most refined and processed biogas is used for Natural Gas Vehicle (NGV) fueling and compressed natural gas (CNG) customers. The least processed entails removal of entrained liquids and increasing the gas pressure. Such minimally processed gas is usable for plant furnace type heating. Intermediate between these stages are 1) the sulfurous and siloxane removal stages which create a product suitable for use in combustion engines for electrical generation, and 2) the pressurization, drying and $CO_2$ removal stage for a product that can be blended with conventional pipeline gas.

The raw biogas is fed through input 16 to a knock-out drum 18. The raw biogas may be extracted from a landfill or digester and, as a result, typically is at negative or very low pressure. The raw biogas may or may not have a feed into analyzer 10.

For biogas extracted at negative or very low pressure, a low pressure blower/pump 20 pressurizes the gas to about 5-7 psi treatment which passes through a heat exchanger 22 to remove the heat generated by compression and then through a coalescing filter 24 for removal of additional moisture. At this point the raw biogas has been sufficiently but minimally processed for use for plant heating and the like. The gas is also subject to analysis by being fed through feed line 26 to the solenoid actuated control valve 14 for input through feed line 12 into the analyzer units of biogas from a raw biogas source.

When the extracted biogas sample is at medium or high pressure, a pressure reducing regulator may be associated with the input to the valve 14 to reduce the input pressure to an acceptable level for introduction into the biogas sample conditioning analyzer unit 10.

In order for the extracted biogas to be capable of being used for powering combustion engines to generate electricity, and in order to prevent damage to the engines and reduce harmful sulfurous deposits, the low pressure gas is passed through $H_2S$ scrubber 28 and siloxane (Si—O—Si) scrubber 30. The now-scrubbed low pressure gas can be fed to the engines and a sample extracted and passed to the analyzer 10 via feed line 32, valve 14 and feed line 12.

If the extracted biogas is not intended for electrical generation but for producing a refined biogas intended to be blended with pipeline quality gas, LNG storage after liquification, or use in fuel cells, the pressure of the now-sulfur and siloxane scrubbed gas is increased to about 150 psi by pump 34 and the pressurized gas fed through a heat exchanger 36 to remove the heat of compression and into a coalescing dryer 38 for moisture removal before moving through a $CO_2$ removal tower array 40 to meet customer specifications. The quality of the processed biogas from this stage is confirmed providing a sample through feed line 42 to valve 14 and feed line 12 into the analyzer 10. The processed biogas is taken off through output 44.

The dehydrated, filtered, $H_2S$, siloxane, $O_2$, $CO_2$, VOC scrubbed, medium pressurized gas (150 psi) can also be fed to and pressurized to about 6000 psi by high pressure pump 46 fed through a high pressure line 48 to dryer 50. The high pressure output is drawn off by outlet 54 form which samples for analysis are fed through line 52 directly to a pressure regulator in the analyzer station 10 for sample analysis. The aforementioned pressurization of the dehydrated, filtered, $H_2S$, siloxane, $O_2$, $CO_2$, VOC scrubbed, medium pressurized gas (150 psi) constitutes an ultimate biogas processing stage required for the product to meet standards such as ISO 15404-2006 for compressed-natural-gas vehicle equipment (NGV and CNG).

Figure 2:
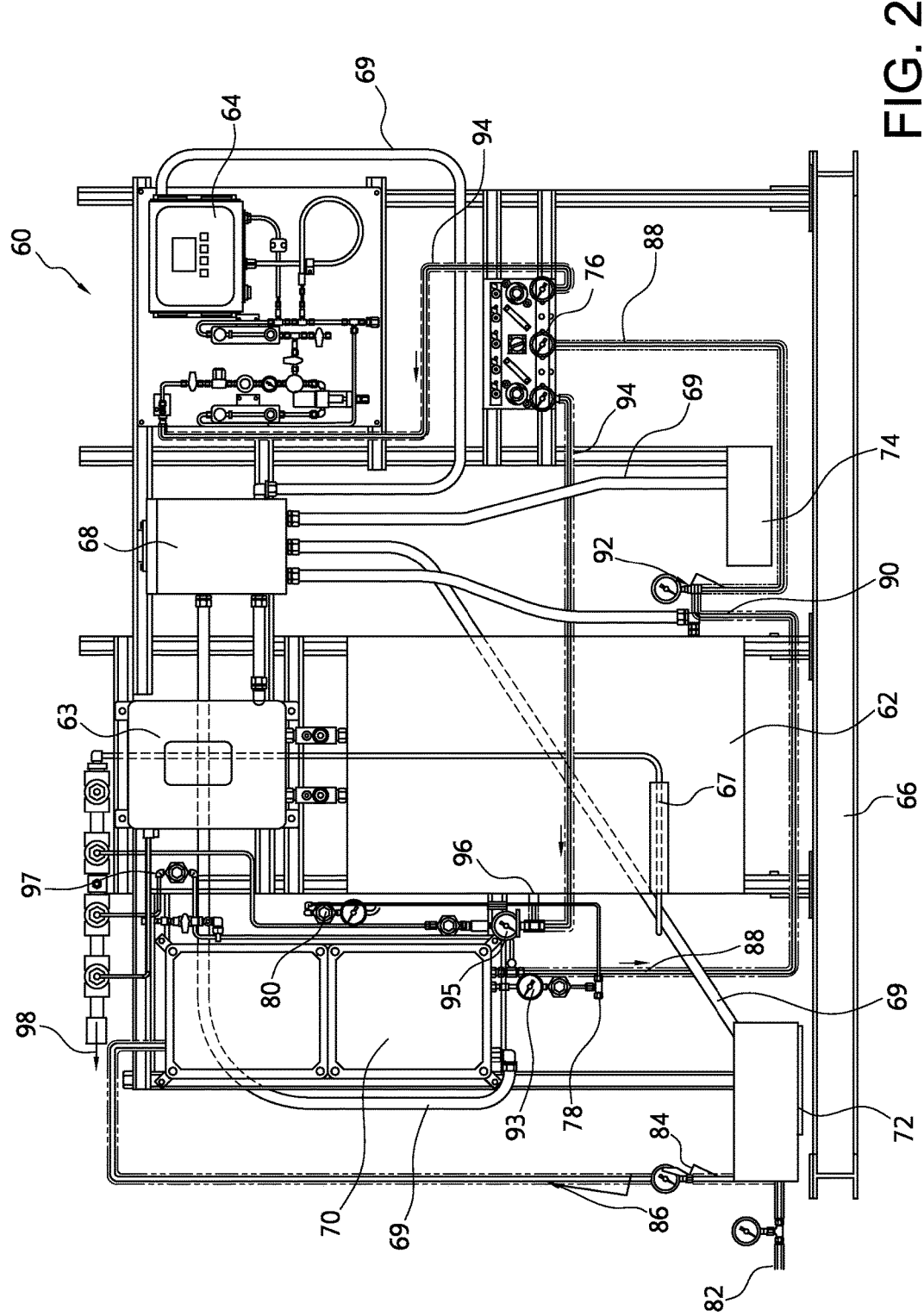
FIG. 2 is a schematic illustration of an embodiment of the invention for conditioning biogas samples initially at negative or insufficient positive pressure for analysis and including both TLD and PID type analyzers.

Turning now to particular disclosed embodiments, reference is first made to FIG. 2 which illustrates a two pump system useful when the extracted biogas sample is at negative or near zero pressure, as typically is the case with, for example, a landfill. The biogas sample conditioner embodiment 60 of FIG. 2, which may or not be enclosed, is configured for mid-grade/intermediate-level gas analysis. The mid-grade/intermediate-level gas analysis is accomplished by a combination of a Tunable Laser Diode TLD analyzer 62 capable of analyzer unit, capable of analytically measuring the required sulfur components of the biogas, with an ionization or IR type analyzer 64 for analyzing siloxane, oxygen, moisture, carbon dioxide, etc., where both analyzers have sensitivity at least to the parts per million (ppm) range. An acceptable Tunable Laser Diode (TDL) unit meeting the functional and operational criteria of the invention is the model SS2100 available from SpectraSensors of Houston, Tex. which includes an input and remote communications control consul unit 63. The Model SS2100 is configurable by a user for concentration measurements and analysis of a select one of a variety of gases including $H_2O$, $CO_2$, $H_2S$, $NH_3$ and $C_2H_2$. It also satisfies NEMA and European operational standards for use in hazardous operational environments.

An acceptable photo ionization type analyzer suitable for use in connection with the invention is a Process Analyzer Model 301C Gas Chromatograph (GC) available from PID, LLC, which provides for chromatographic separation, identification, and quantitation of gaseous chemical components. An alternative is a model OXY4400, a fluorescence quenching based photo ionization detector system available from SpectraSensors.

The unit 60 of FIG. 2 is secured preferably within a containment housing (said housing optionally non-explosion proof) on an appropriately dimensioned steel skid 66. Electrical power can be provided to the components through a conventional 120 V Electrical power distribution panel 68. The power distribution panel 68 distributes power to the analyzers 62 and 64, as well as to a membrane dryer 70, pumps 72 and 74, and a solenoid actuated flow control switch unit 76 via shielded power line conduits 69.

A suitable dryer unit for incorporation in the invention is gas dryer such as a MiniGASS unit from Perma Pure LLC of Toms River, N.J. The MiniGASS system generally contains "tube-in-shell" membrane for water/moisture removal combined with temperature control heating and a coalescing/particulate filter technology and purge flow controls. Preferably the tubes are composed of NAFION®, a Dupont sulfonated tetrafluoroethylene based fluoropolymer-copolymer that is highly selective in the removal of water.

In effect the unit relies on gas pressure differential between the sample gas and a counter-flowing industrial grade (dry) purge gas supplied from a compressor at about 80 psi. Monitoring and maintaining pressure regulation is important particularly in the case of a pressure sensitive dryer construction such as a multi-tube NAFION® gas dryer so as to prevent any adverse impact to the integrity of the tube structure which can be damaged at pressures exceeding 80 psig. In the illustrated embodiment, ½ hp, 200 Watt pumps providing a 6 lpm with the inlet pressure at atmosphere pressure and the outlet at 30 psig to the analyzer is used. The Model No. R201-FP-NA1 Single head, Series R, Dia-Vac® from Air Dimensions, Inc. of Deerfield Beach, Fla., meets this criteria. Instrumentation calibration gas is passed via input line 78 through pressure regulated line 80 at an input pressure of about 60 psi.

Referring to the sample gas flow in FIG. 2, gas is inputted to the gas sample dryer unit 70 at a pressure of about 1 to 7 psi. Following thermal conditioning via a probe takeoff, the gas is drawn via pump 72 from a negative pressure (i.e., −0.97 psi) to a positive pressure of about 5 and up to 7 psi, and passed through dryer intake tube 86 via treated gas input 82 through 2 micron particle filter 84. The dried gas exits the dryer 70 via output tube 88, through the pressure regulator 90 and another 2 micro particle filter 92 to the solenoid valve switch 76. The pressurized, dried, and filtered sample gas is then directed via sample conduits 94 to the appropriate analyzer sample gas input (see element 96 associated with analyzer 62). The gas sample input to the gas analyzer unit can be at a pressure of about 30 psi. Sample return to flare exits the analyzer at output 67 which connects through exhaust lines to vent off to flare excess gas or gas subject to back pressure regulation via exhaust manifold 98.

Figure 3:
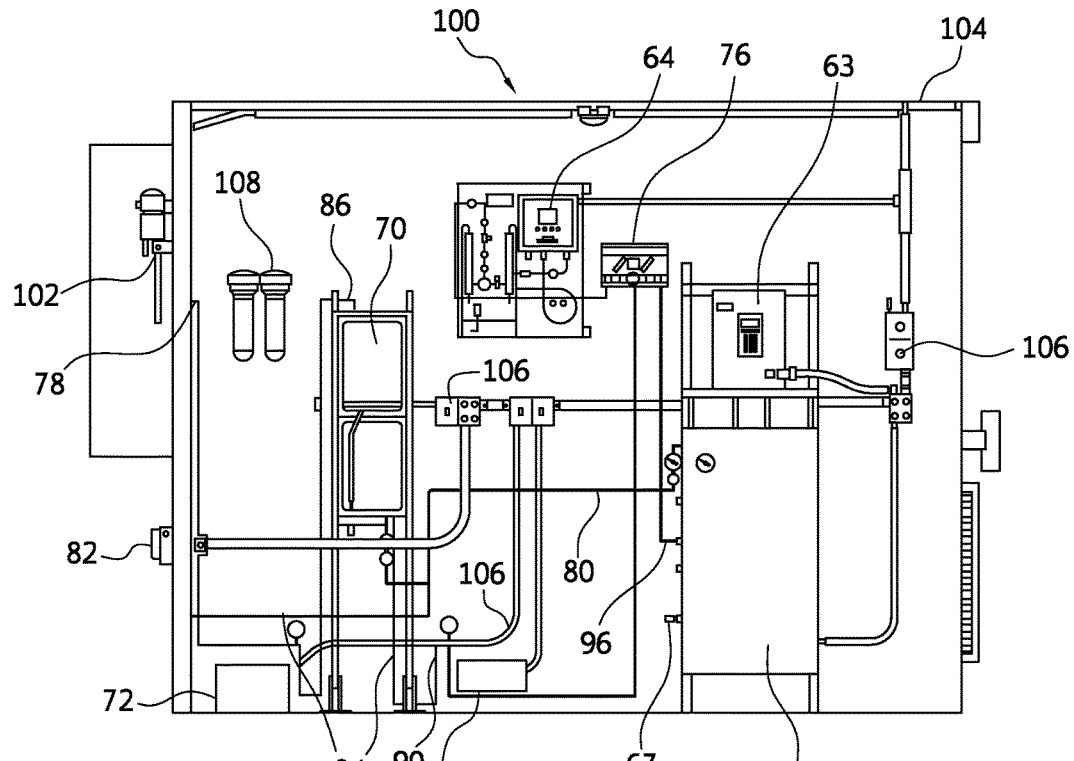
FIG. 3 is a schematic view of the interior of an enclosure containing an embodiment of the invention.

In FIG. 3, a biogas sample conditioning cabinet 100 is illustrated. The cabinet 100, otherwise generally corresponding to the embodiment described above in relation to FIG. 2, contains a Tunable Laser Diode analyzer 62, a fluorescence quenching type gas analyzer 64, an electrical power distribution panel 68, a dryer unit 70, pumps 72 and 74, switching solenoid 76. The extracted gas sample is introduced via input 82 and selectively pressurized by the pumps and associated pressure regulators 84 and 90. Industrial grade purge gas flows from an input 78 at pressures controlled by regulator line 80 to the input of analyzer 62.

Instrument calibration gas (i.e., Nitrogen) is provided from a tank connected to tank regulator 102. Inside the cabinet 100, electrical power is introduced to the various components and the internal cabinet heater via conduit 104 and the array of associated control switches 106. As an option, the cabinet may be connected to an external compressor for generating the industrial grade air. In that case, compressor intake dryer filters 108 may be affixed within the cabinet interior which facilitates user filter maintenance.

Figure 4:
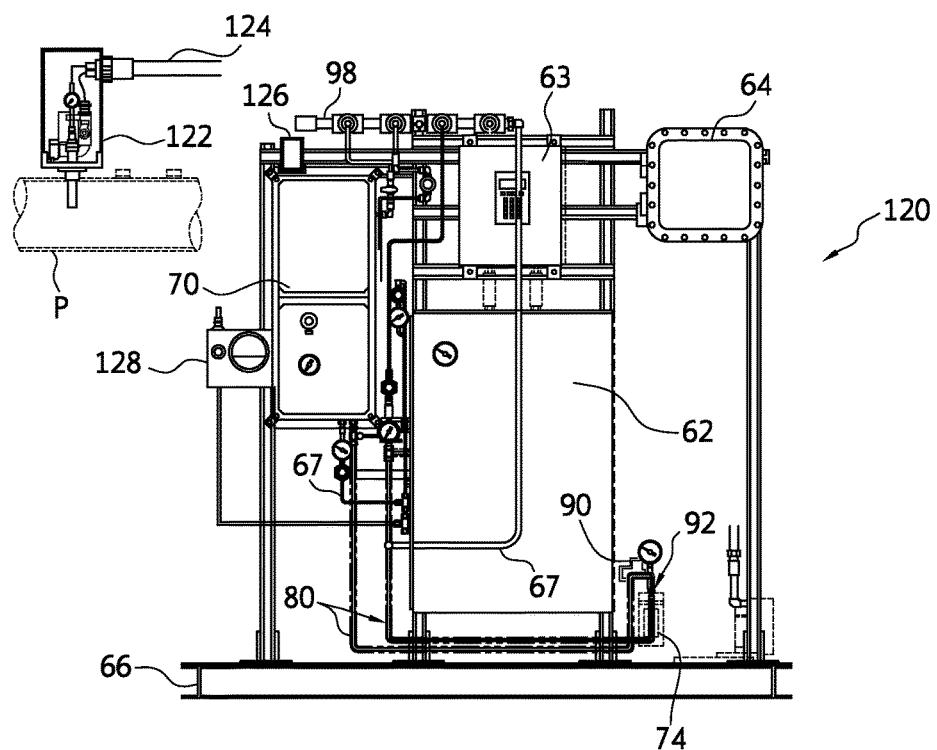
FIG. 4 is a schematic illustration of an alternate embodiment of the invention for conditioning samples of biogas at adequate positive pressure.

FIG. 4 is representative of an embodiment of the invention 120 employable where the target biogas product is under positive pressure (at least about 5 psi) at the takeoff, and where the intended end use of the gas requires an intermediate level analysis. That is to say that the scrubbed biogas will be used for no more than electrical power generation by internal combustion. As a result, the need for an ionization or fluorescence quenching type gas analyzer is minimized.

A heated enclosure 122 for a probe directly mounted to a pipeline P for gas sampling. As illustrated in Applicant's U.S. Pat. No. 7,162,933, herein incorporated by reference in its entirety, the enclosure 122 provided is typically electrically heated, which serves to maintain temperature stability of the gas sample and avoid dew point dropout resulting from Joule-Thompson type condensation as it travels from its extraction point (i.e., a natural gas liquid line probe) through a small diameter stainless steel tubing sample gas line 124, which itself is thermally shielded with heat tracing to maintain thermal stability of the sample. The sample tubing 124 projects through the cabinet wall (not illustrated in FIG. 4) to the input 126 of the dryer unit 70. From the dryer unit output, the dried gas sample travels through insulated, gas line 80 through regulator 90, and filter 92 to the input port of the analyzer 62. Compressed instrument air (or inert gas) to the analyzer instrument and system is controlled by a Z-purge pressurization unit 128 such as the BEPCO EPS Model 1001A from Pepperl+Fuchs, Inc. (Twinsburg, Ohio) which provides a hazardous condition enclosure-by-pressurization-or-purging system that regulates and monitors pressure within the cabinet containing unit 120. Surplus gas is vented to flare through manifold 98, as described above in connection with the first embodiment. In summary, the embodiment of FIG. 4 includes only the single analyzer for receiving extracted gas samples at positive pressure, therefore dispensing with need for a pre-dryer pump and an internal multipath solenoid valve.

Figure 5:
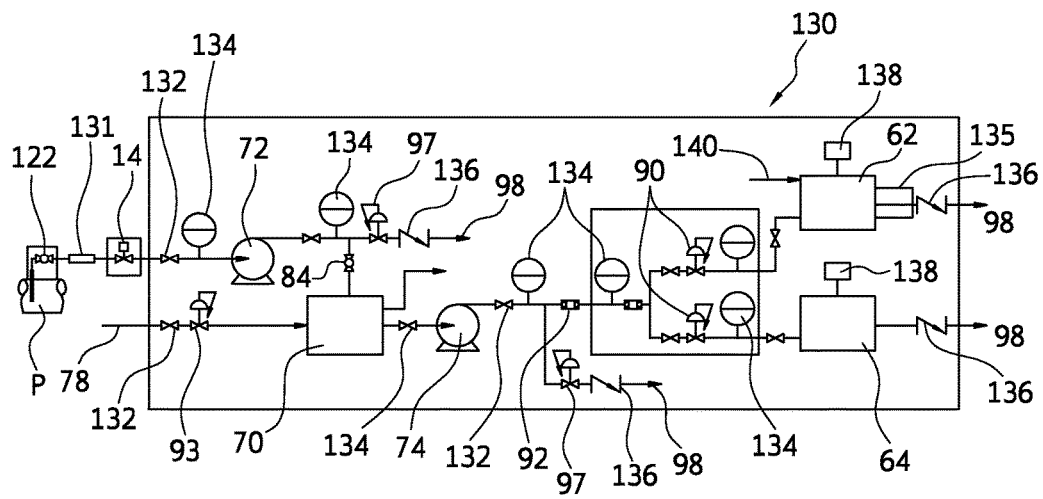
FIG. 5 is a pressure and flow diagram including valves, filters, and regulators corresponding to the embodiment of FIG. 2.

Turning to FIG. 5, it represents a process flow diagram 130 of the gas sample and compressed instrument grade gas and instrument calibration gas. Reference is made particularly to FIG. 2 for corresponding elements. The sample gas is extracted from pipeline P and heated in enclosure 122 before moving through a feedline, which in this case is associated with electrical heat tracing 131. The gas sample passes via vacuum or low pressure through the inflow solenoid switch 14 to the analyzer cabinet through an in-line valve 132 and pressure regulator 134 and pressurized up to 10 psi by pump 72.

The now-pressurized gas passes through filter 84 and into the dryer 10 or is passed through pressure reducing regulator 97 through a one way check valve 136 to flare/sample return manifold 98. The filtered sample gas passing through the dryer passes through an in line valve 132, and is further pressurized to about 30 psi by pump 74. The further pressurized gas then passes through another in line valve 132 and regulator 134 either to the filter 92 or to sample return pressure reducing regulator 97. If the pressurized gas is passed to sample return/flare manifold 98 through reducing regulator 97, backflow is prevented by in-line check valve 136. If the pressurized gas is passed onto for analysis, the sample passes through a further particulate filter, the pressure regulator 90, and into a select one of the analyzer units 62 or 64. Calibration gas is supplied independently via supply 138 to the respective analyzer unit.

Referring to the path of the instrument grade pressurized purge gas, it typically enters the cabinet through port line 78 at about 80 psi, passes through an in line valve 132 and through pressure reducing regulator 93 to dryer 70 at about 30 psi or passes directly to the analyzer 62 through regulator 80 and input 140 at about 60 psi input pressure. The analyzer 62 provides alternative outlet pathways 135 (bypass, output, and relief) through a check valve 136 to sample return/flare manifold 98. In this illustration, the analyzer 64 includes only a single output for the sample to the sample return flare 98 through the one-way check valve 136.

Figure 6:
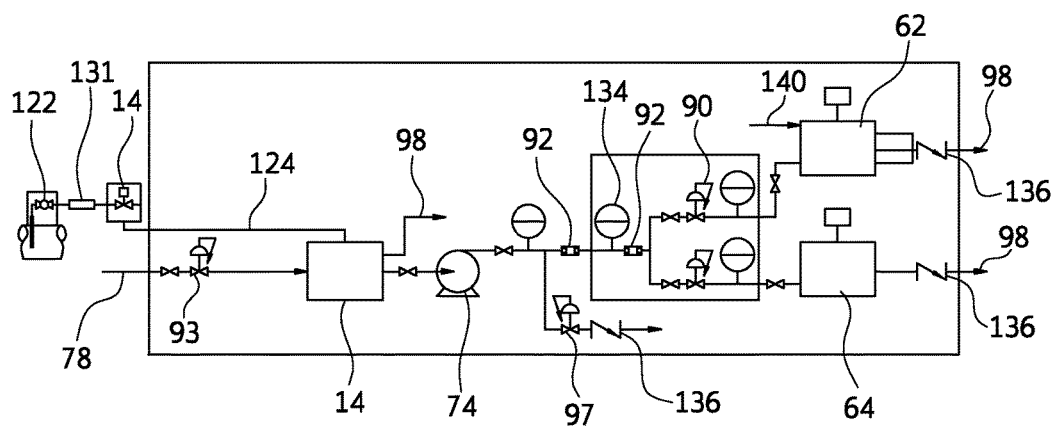
FIG. 6 is a pressure and flow diagram including valves, filters, and regulators corresponding to a positive pressure biogas source embodiment.

Turning to FIG. 6, it represents a process flow diagram of a biogas sample which at takeoff is at positive pressure. In short, this embodiment dispenses with the need of pre-drying pressurization such as that illustrated in FIG. 4.

The invention has been disclosed in the forgoing specification. It is understood by those skilled in the art that many modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

I claim:

1. A system for conditioning and analyzing a low pressure biogas pipeline stream where the biogas contains one or more contaminants selected from the group consisting of $H_2O$, $CO_2$, $H_2S$, $NH_3$, $C_2H_6$, siloxanes, VOC, and $O_2$ intermixed with $CH_4$, said system, comprising:
   a) at least a first gas pipeline takeoff probe for extracting a biogas sample, a heated probe housing, a biogas communication line limiting dew point dropout of the biogas sample conveying the heated biogas sample to a solenoid controlled valve switch and into a sample analyzer cabinet;
   b) a gas dryer unit for receiving the extracted biogas sample;
   c) a pump and a pressure regulator for increasing the pressure of the heated biogas sample exiting the gas dryer;
   d) a gas analyzer unit for measuring the quantity of a contaminant selected from the group consisting of $H_2O$, $CO_2$, $H_2S$, $NH_3$, siloxanes, VOC, and $O_2$ present in the dried and pressurized and heated, biogas sample;
   e) a source of compressed industrial grade purge gas input, said purge gas being passed through a pressure regulator to said gas dryer unit and said gas analyzer unit; and
   f) a gas exhaust for venting the analyzed biogas sample.

2. The system according to claim 1 further including a solenoid actuated input switch for selecting a particular output from a biogas scrubbing array.

3. The system according to claim 2 further including an in-line particulate filter associated with said first pressure regulator.

4. The system according to claim 2 where the gas sample input to the gas sample dryer unit is at a pressure of 1-7 psi.

5. The system according to claim 4 where the gas sample input to the gas analyzer unit is at a pressure of 30 psi.

6. The system of claim 2 where the biogas at the point of extraction is at negative pressure, said system further including an extraction pump and associated pressure regulator for increasing the pressure to positive of the extracted biogas sample prior to introduction into a gas dryer unit.

7. The system according to claim 6 where the gas sample input to the gas analyzer unit is at a pressure of 30 psi.

8. The system according to claim 5 where the gas exhaust is vented to flare.

9. A system for conditioning and analyzing a sample extracted from at least one stream of a biogas where the biogas contains one or more contaminants selected from the group consisting of $H_2O$, $CO_2$, $H_2S$, $NH_3$, $C_2H_6$, siloxanes, VOC, and $O_2$ intermixed with $CH_4$, said system, comprising:
   a) at least a first gas pipeline takeoff probe for extracting a low pressure biogas sample, a heated probe housing, a biogas communication line limiting dew point dropout of the biogas sample conveying the heated biogas sample to a solenoid controlled valve switch and into a sample analyzer cabinet;
   b) a first pump and a first pressure regulator for increasing the pressure of the heated gas sample for introduction into a gas dryer unit;
   c) a second pump and a second pressure regulator for further increasing the pressure of the heated gas sample exiting the dryer;
   d) a gas analyzer unit for measuring the quantity of a contaminant selected from the group consisting of $H_2O$, $CO_2$, $H_2S$, $NH_3$, $C_2H_6$, siloxanes, VOC, and $O_2$ present in the dried and pressurized and heated, biogas sample;
   e) a source of compressed industrial grade purge gas input gas passed through a pressure regulator to gas dryer unit and said gas analyzer unit; and
   f) a gas exhaust for venting the analyzed biogas sample.

10. The system according to claim 9 further including a solenoid actuated input switch for selecting a particular output from a biogas scrubbing array.

11. The system according to claim 10 further including an in-line particulate filter associated with said first pressure regulator.

12. The system according to claim 11 where the gas sample input to the gas sample dryer unit is at a pressure of 1-7 psi.

13. The system according to claim 12 where the gas sample input to the gas analyzer unit is at a pressure of 30 psi.

14. The system according to claim 9 where the gas exhaust is vented to flare.

15. A method for conditioning a biogas sample for confirmation of its quality, comprising the steps of:
   extracting a biogas sample from a select source;
   regulating the temperature and pressure of the extracted biogas sample;
   feeding the pressure and temperature regulated biogas sample into a dryer for removal of moisture;
   increasing the pressure of the biogas sample output from the dryer;

feeding said biogas sample to a dryer gas component analyzer for measuring the component in the biogas sample; and selecting a particular of multiple biogas sample source feeds for feeding to the dryer.

16. The method of claim 15 further including the steps of purging the biogas sample from the dryer and introducing a fresh sample to the dryer.

17. The method of claim 16 further including the step of venting the biogas sample from the analyzer to flare.

* * * * *